United States Patent [19]
Stein et al.

[11] Patent Number: 6,060,504
[45] Date of Patent: May 9, 2000

[54] N-METHYL-N-[(1S)-1-PHENYL-2-(3S)-HYDROXYPYRROLIDIN-1-YL)ETHYL]-2-2-DIPHENYLACETAMIDE

[75] Inventors: Inge Stein, Rodgau; Holger Beeres, Crumstadt; Klaus Beschmann, Reinheim; Steffen Neuenfeld, Messel; Andrew Barber, Weiterstadt, all of Germany

[73] Assignee: Merck Patent Gesellschaft mit Beschrankter Haftung, Germany

[21] Appl. No.: 08/703,350

[22] Filed: Aug. 26, 1996

[30] Foreign Application Priority Data

Aug. 26, 1995 [DE] Germany .................... 195 31 464

[51] Int. Cl.⁷ .................... A61K 31/40; C07D 207/12
[52] U.S. Cl. .................... 514/428; 548/453; 548/568
[58] Field of Search .................... 514/428; 548/453, 548/568

[56] References Cited

U.S. PATENT DOCUMENTS 5,532,266  7/1996  Gottschlich et al. .................... 514/428

FOREIGN PATENT DOCUMENTS 4215213  5/1992  Germany .................... 207/36

OTHER PUBLICATIONS

Haleblian, John K., "Characterization of Habits and Crystalline Modification of Solids and Their Pharmaceutical Applications", *Journal of Pharmaceutical Sciences*, vol. 64, No. 8, pp. 1269–1288 (Aug. 1975).

Haleblian, John K., et al., "Pharmaceutical Applications of Polymorphism", *Journal of Pharmaceutical Sciences*, vol. 58, No. 8, pp. 911–929 (Aug. 1969).

Gottschlich, R., et al., "EMD 61753 As a Favourable Representative of Structurally Novel Arylacetamido–Type K Oplate Receptor Agonists", *Bioorganic & Medicinal Chemistry Letters*, vol. 4, No. 5, pp. 677–682 (1944).

Gottschlich, R., et al., "K–Opioid Activity of the Four Stereoisomers of the Peripherally Selective k–Agonists, EMD 60 400 and EMD 61 753", *Chirality* 6:685–689 (1994).

Pearson, J.T., et al., "The Influence of Crystal Structure on Drug Formulation", *Manufacturing Chemist*, vol. 44, No. 12 (Jan. 15, 1974).

*Primary Examiner*—Johann Richter
*Assistant Examiner*—Jane C. Osswecki
*Attorney, Agent, or Firm*—Millen, White, Zelane, & Branigan, P.C.

[57] ABSTRACT

The invention relates to a novel heat-stable form of N-methyl-N-[(1S)-1-phenyl-2-((3S)-3-hydroxypyrrolidin-1-yl)ethyl]-2,2-diphenylacetamide and to a process for the preparation and isolation of this compound in this novel form and to use for the production of medicaments which contain this compound and/or one of its physiologically acceptable salts.

7 Claims, No Drawings

N-METHYL-N-[(1S)-1-PHENYL-2-(3S)-HYDROXYPYRROLIDIN-1-YL)ETHYL]-2-2-DIPHENYLACETAMIDE

BACKGROUND OF THE INVENTION

The present invention relates to a novel heat-stable form of N-methyl-N-[(1S)-1-phenyl-2-((3S)-3-hydroxypyrrolidin-1-yl)ethyl]-2,2-diphenylacetamide and to a process for the preparation and isolation of this compound in this novel form and to use for the production of medicaments which contain this compound and/or one of its physiologically acceptable salts.

Compounds of this structural formula and also the abovementioned compound and suitable processes for their preparation are described in the Offenlegungsschrift DE 42 15 213 A1.

It has been found that the compound N-methyl-N-[(1S)-1-phenyl-2-((3S)-3-hydroxypyrrolidin-1-yl)ethyl]-2,2-diphenylacetamide, which is already known from Patent Application DE 42 15 213 A1, is a pharmaceutically particularly active compound which is very particularly suitable as a medicament for the treatment of inflammatory bowel disorders. In particular, this compound can be employed and is effective in this indication, as it simultaneously alleviates the pain associated with this disorder and in the acute case of an intestinal occlusion threatening or produced by the inflammatory bowel disorder again normalizes the motility of the intestine or sets it in motion again without causing noticeable side effects.

Attempts to prepare this compound according to the process known from DE 42 15 213 A1 have shown that this compound is obtained in various forms.

Thus, it was desirable to make available N-methyl-N-[(1S)-1-phenyl-2-((3S)-3-hydroxypyrrolidin-1-yl)ethyl]-2,2-diphenylacetamide in heat-stable form and to provide a process for the preparation of this compound, by means of which a heat-stable product is obtained which is stable on storage and suitable for the production of pharmaceutical formulations.

SUMMARY OF THE INVENTION

The invention thus relates to heat-stable, storable N-methyl-N-[(1S)-1-phenyl-2-((3S)-3-hydroxypyrrolidin-1-yl)ethyl]-2,2-diphenylacetamide and to its use as a medicament for the treatment of inflammatory bowel disorders and also to pharmaceutical preparations which contain this compound as a constituent and can therefore be employed for the effective treatment of inflammatory bowel disorders and the disease symptoms associated therewith, and for the treatment of severe pain, in particular, of hypersensitivity to pain.

The invention likewise relates to the use of this compound as a medicament for the treatment of pain and hypersensitivity to pain occurring in back complaints, burn injuries, sunburn and rheumatic disorders and also inflammatory reactions occurring in this context. The invention also relates to the use of this medicament for the treatment of post-operative pain, hypersensitivity reactions to pain and the ileus frequently occurring after abdominal operations. The invention further relates to the use of the corresponding compound in pharmaceutical formulations for the treatment of neurodermatitis.

This invention moreover relates to a process for the preparation of heat-stable, storable N-methyl-N-[(1S)-1-phenyl-2-((3S)-3-hydroxypyrrolidin-1-yl)ethyl]-2,2-diphenylacetamide.

Upon further study of the specification and appended claims, further objects and advantages of this invention will become apparent to those skilled in the art.

The compound according to the invention and its physiologically acceptable salts exhibit particularly good analgesic actions. In this connection, they antagonize, in particular, inflammation-related hyperalgesias but are also effective in the control of the actual inflammatory event, so that they have a broad spectrum of action.

Experiments have shown that the compound according to the invention is active in the "writhing test" on mice or rats (method cf. Siegmund et al., Proc. Soc. Exp. Biol. 95, (1957), 729–731). The analgesic action as such can be further demonstrated in the "tail-flick test" on mice or rats (methodology cf. d'Amour and Smith, J. Pharmacol. Exp. Ther. 72, (1941), 74–79) and further in the "hot plate test" (cf. Schmauss and Yaksh, J. Pharmacol. Exp. Ther. 228, (1984), 1–12 and the literature cited there). Particularly strong actions are to be observed on rats in the carrageenan-induced hyperalgesia model (cf. Bartoszyk and Wild, Neuroscience Letters 101 (1989) 95). In this context, this compound shows no or only a small tendency to physical dependence.

Additionally, by means of corresponding experiments carried out by familiar methods, pronounced anti-inflammatory, diuretic, anticonvulsive and neuroprotective actions were demonstrated. The compound exhibits a high affinity with respect to the binding behavior to kappa-receptors.

In contrast with other compounds having a similar spectrum of action, the compound according to the invention is particularly suitable for use in pharmaceutical preparations for the treatment of inflammatory bowel disorders, as in addition to the analgesic and anti-inflammatory action it is suitable for normalizing disorders of the intestinal motility produced by the disorder. In particular, it is suitable for getting the bowel movements going again if, due to the inflammatory bowel disorder, intestinal obstruction threatens or has already occurred. This action can also be employed for the treatment of postoperative ileus and the pain associated therewith.

Due to the pharmacological activities described above, the compound according to the invention has proved particularly suitable in the treatment of burns, namely both of burns due to the action of heat or flames and also of severe sunburn. In particular, in addition to the actual pain and hypersensitivity reactions to pain, inflammatory processes can additionally be influenced in these indications by the administration of suitable pharmaceutical preparations which comprise the active compound according to the invention. Also, the reflex ileus occurring in the case of the most severe burns can be prevented or treated.

In this connection, indications have also been found which point to an advantageous action in the treatment of allergies to the sun, especially as under the influence of the compound according to the invention allergic skin reactions rapidly fade and the itching associated therewith rapidly subsides. Corresponding positive results were also found in the treatment of neurodermatitis. In particular, the itching of the skin in this disorder subsides under the action of the above-mentioned active compound and inflammatory reactions occurring due to the disorder are favorably influenced.

Furthermore, this active compound has proved particularly effective in the treatment of rheumatic disorders and of back conditions. It is particularly advantageous in this connection that it is both active against the pain associated therewith and positively affects the inflammatory processes occurring in rheumatic disorders and thus contributes to an improvement in the general condition of the patient. In this context, it has advantageously been shown that normal motility of the gastrointestinal tract is not adversely affected.

In all indication areas described here, the use of N-methyl-N-[(1S)-1-phenyl-2-((3S)-3-hydroxypyrrolidin-1-yl)ethyl]-2,2-diphenylacetamide hydrochloride as a medicament has emerged as particularly effective in all types of preparation forms.

Chemical and physical investigations for the characterization of this compound according to the invention have shown that it is contained in various forms, depending on preparation and storage.

In detail, to date four different crystal forms have been found which differ from one another significantly. Type 1 is a solvate. This form is readily converted into another crystal type which is designated in the following text as type II. On slow heating of type I, a release of solvent takes place. The X-ray diffractometry, IR analysis and the melting point data then correspond to those of type II.

The compound prepared by the previously known process described in the earlier application DE 4215 213 A1 is obtained as type II and has a melting range of 196–200° C. (see also Bioorganic & Medicinal Chemistry Letters 4 (5), 679 (1994) and has a heat of fusion of 100 J/g.

A form designated as type III is obtained if type II is stored under extreme conditions at an atmospheric humidity of approximately 73% to 95%.

A modification characterized in the following as type IV has, compared with that of type II, a melting range of approximately 221–226° C. and a heat of fusion of approximately 120–128 J/g.

The higher melting point and the higher heat of fusion of the compound according to the invention show that the thermodynamically stable crystal form is present, the two crystal forms II and IV obtained being monotropic to one another.

This state of affairs can be confirmed by further observations. On very rapid cooling of a melt obtained from the thermodynamically unstable type II crystal form (m.p. 196–200° C.) from 210° C. to −78° C. and storage at −78° C. for five hours the thermostable compound (221–226° C.) slowly crystallizes out.

In the case of these two types, not only their melting behavior differs but also their storage stabilities. After storage of type II crystals in a drying oven at 170° C., a partial conversion into type IV was detected. During DSC determination (DSC=Differential Scanning Calorimetry) of the crystal form of type II, on slow heating above the melting point at approximately 200° C. the crystal type IV which melts at approximately 220–226° C. crystallizes out. Crystal type IV is also detected when a melt of type II (just above 200° C.) is suddenly cooled and stored at room temperature for a period of 12 to 16 hours. While type II has therefore proved to be metastable, type IV is a thermodynamically stable form. By means of specific crystallization tests, it was found that by addition of seed crystals of type IV only the crystal form IV is obtained. In contrast to this, however, by seeding with seed crystals of type II the crystal form IV is especially obtained. Additionally, the solubility of the crystal type IV in aqueous solution is lower than that of type II. It has approximately 45% to 70% of the solubility of type II.

After seven months' storage of the compound prepared by the process described in the earlier application DE 4215213 A1 at room temperature, it was possible to determine a start of conversion to the thermostable crystal modification IV. That is to say the compound prepared by the process described in this invention is stable on storage in contrast to the other crystal form.

In the presence of solvents (e.g., water), the compound prepared can form solvates.

When using the compound according to the invention with the crystal form of the type II in pharmaceutical formulations, on relatively long storage a change in the crystal forms can occur.

Previous investigations of the pharmaceutical activity have so far shown it to be relatively independent of the crystal form which, however, does not exclude differences due to a possible modified bioavailability. For use in solid pharmaceutical formulations, care must therefore be taken that the stable crystal form of the type IV is employed or that when using the type II form, additives are employed by means of which a long-term stabilization of this crystal type is effected.

Surprisingly, it now appeared that not only the manner of working up of the crude product obtained by the actual reaction has an influence on the crystal form but that even the conditions under which the starting materials react with one another are important for this. It was found that in this case, in particular, the reaction temperatures and the solvent conditions play a part.

In detail, it has been shown that crystallization form type IV is obtained if the reaction of the starting materials 1-[(1S)-3-hydroxypyrrolidin-1-yl]-(2S)-2-methylamino-2-phenylethane and diphenylacetyl chloride is carried out at low temperatures, in particular, at −5 to 10° C., preferably at 0 to 8° C.

It has furthermore proved advantageous for this purpose that the molar ratio of the starting materials 1-[(1S)-3-hydroxypyrrolidin-1-yl]-(2S)-2-methylamino-2-phenylethane and diphenylacetyl chloride to one another is 1:0.75 to 1:1.65, preferably 1:1.1 to 1:1.3.

The molar ratio of the starting compounds 1-[(1S)-3-hydroxypyrrolidin-1-yl]-(2S)-2-methylamino-2-phenylethane and diphenylacetyl chloride to the solvent used should in this case be selected such that the starting materials are in solution but the solvent, if possible, is present only in a small excess. If tetrahydrofuran is selected as a solvent, it has proved advantageous if the molar ratio of the above-mentioned starting materials and the solvent to one another is approximately (0.8–1.2):(0.9–1.3):(14–22). A ratio of (0.9–1.1):(1–1.2):(16–19) has particularly effective.

A very slow addition of the diphenylacetyl chloride dissolved in one part of the solvent used has proved particularly advantageous, namely in particular while maintaining a low temperature. To complete the reaction, stirring is continued for some time at the same temperature but, if possible, for not longer than approximately four hours. A period of stirring of 1.5 to 2.5 hours has emerged as optimum.

To purify the crude product obtained in this manner, it is recrystallized from a suitable solvent. In this context, it is advantageous to select the amount of solvent such that the product crystallizes, even in the hot solvent.

When using ethanol, this is achieved at molar ratios of approximately one mol of product relative to 75 to 125 mol, in particular, 85 to 115 mol of solvent.

Depending on the choice of the solvent from which it is recrystallized, the purified product is precipitated in crystalline form in the modification of the type IV even after brief cooling. When using ethanol, it is the case after cooling to temperatures of approximately 55 to 45° C. It has proved advantageous in this case to maintain this temperature during the entire crystallization.

It has proved particularly advantageous in the case of the compound according to the invention that it obviously cannot pass through the blood-brain barrier, due to its structure, and therefore exhibits no dependence potential. Also, thus far no side effects have been found which would restrict the use of the advantageous actions for the claimed indications in any way.

The compound according to the invention and its physiologically acceptable salts can therefore be used for the production of pharmaceutical preparations by bringing them into the suitable dose form together with at least one excipient or auxiliary and, if desired, with one or more further active compounds. The preparations thus obtained can be employed as medicaments in human or veterinary medicine. Suitable excipients are organic or inorganic substances which are suitable for enteral (e.g., oral or rectal) or parenteral administration and do not react with the novel compound; for example, water, vegetable oils, benzyl alcohols, polyethylene glycols, glycerol triacetate and other fatty acid glycerides, gelatin, soya lecithin, carbohydrates such as lactose or starch, magnesium stearate, talc or cellulose.

For oral administration, in particular, tablets, coated tablets, capsules, syrups, juices or drops are used. Of interest are specially coated tablets and capsules having enteric coatings or capsule shells. For rectal administration, suppositories are used and for parenteral administration, solutions, preferably oily or aqueous solutions and also suspensions, emulsions or implants are used.

The active compound claimed, according to the invention, can also be lyophilized and the lyophilizate obtained used, for example, for the production of injection preparations.

The preparations indicated can be sterilized and/or contain auxiliaries, such as preservatives, stabilizers and/or wetting agents, emulsifiers, salts for affecting the osmotic pressure, buffer substances, colorants and/or flavorings. If desired, they can also contain one or more further active compounds, e.g., one or more vitamins, diuretics or anti-inflammatories.

The compound I, according to the invention, is generally administered in analogy to other known preparations available commercially for the indications claimed, preferably in doses of between about 1 mg and 50 mg, in particular, between 5 and 30 mg per dose unit. The daily dose is preferably between about 0.02 and 20 mg/kg, in particular, 0.2 and 0.4 mg/kg of body weight.

The specific dose for each individual patient depends, however, on all sorts of factors; for example, on the age, body weight, general state of health and sex, on the diet, on the time and route of administration and on the excretion rate, pharmaceutical combination and severity of the particular disorder to which the therapy applies. Oral administration is preferred.

In the following, examples are given which serve to illustrate the invention but do not restrict the invention to the examples given.

In the following text, all temperatures are indicated in °C.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding application No. DE 19531464.6, are hereby incorporated by reference.

EXAMPLES

Comparison Example
N-methyl-N-[(1S)-1-phenyl-2-((3S)-3-hydroxypyrrolidin-1-yl)ethyl]-2.2-diphenylacetamide hydrochloride (type II)

22 g of 1-(1S)-3-hydroxypyrrolidin-1-yl]-(2S)-2-methylamino-2-phenylethane are initially introduced into a 500 ml apparatus and dissolved in 150 ml of tetrahydrofuran. While stirring, a solution consisting of 150 ml of tetrahydrofuran and 24.1 g of diphenylacetyl chloride is added dropwise at 10–20° C. in the course of one hour, a precipitate being formed at the start which, however, goes into solution again in the course of the reaction. Towards the end of the reaction, a precipitate is again formed. The mixture is stirred at room temperature for a further 12 hours. It is then cooled to about 5° C., and the precipitated product is filtered off with suction. The separated product is washed with about 100 ml of tetrahydrofuran and dried. In this way, 39 g of crude product are obtained. This is recrystallized using about 250 ml of ethanol and 1 g of active carbon.

Yield: 33 g of N-methyl-N-[(1S)-1-phenyl-2-((3S)-3-hydroxypyrrolidin-1-yl)ethyl]-2,2-diphenylacetamide hydrochloride (73.2% of theory).

Melting point: 196–200° C.
Heat of fusion: 100 J/g.
$pK_a$: 7.4.
Solubility in water at 20° C.: 1.16 g/100 ml.
Solubility in methanol at 20° C.: 6.31 g/100 ml.

Example 1
N-methyl-N-[(1S)-1-phenyl-2-((3S)-3-hydroxypyrrolidin-1-yl)ethyl]-2,2-diphenylacetamide hydrochloride (type IV)

A solution consisting of 10.5 g of diphenylacetyl chloride and 17 ml of tetrahydrofuran is slowly added dropwise with stirring in the course of 75 minutes to a reaction solution, cooled to 0 to 8° C., consisting of 9 g of 1-[(1S)-3-hydroxypyrrolidin-1-yl]-(2S)-2-methylamino-2-phenylethane and 40 ml of tetrahydrofuran. The mixture is then stirred at the same temperature for a further 120° minutes. The reaction product depositing in the course of this as a precipitate is filtered off with suction and dried. In this manner, 17 g of crude product are obtained which are recrystallized from 180 ml of ethanol. During this recrystallization, the product prepared is deposited at 50° C. as the stable crystal type IV.

Yield: 13 g of N-methyl-N-[(1S)-1-phenyl-2-((3S)-3-hydroxypyrrolidin-1-yl)ethyl]-2,2-diphenylacetamide hydrochloride (70.6% of theory).

Melting point: 221–226° C.
Heat of fusion: 124 J/g.
$pK_a$: 7.4.
Solubility in water at 20° C.: 0.76 g/100 ml.
Solubility in methanol at 20° C.: 4.26 g/100 ml.

The following examples relate to pharmaceutical preparations:

Example A

Injection Vials

A solution of 100 g of the active compound and 5 g of disodium hydrogen phosphate are adjusted to pH 6.5 in 3 l of double-distilled water using 2N hydrochloric acid, sterile filtered, filled into injection vials, lyophilized under sterile conditions and aseptically sealed. Each injection vial contains 5 mg of active compound.

Example B

Suppositories

A mixture of 20 g of the active compound is fused with 100 g of soya lecithin and 1400 g of cocoa butter, poured into molds and allowed to cool. Each suppository contains 20 mg of active compound.

Example C

Solution

A solution is prepared from 1 g of an active compound of the formula I, 9.38 g of $NaH_2PO_4.2H_2O$, 28.48 g of $NA_2HPO_4.12H_2O$ and 0.1 g of benzalkonium chloride in 940 ml of double-distilled water. The solution is adjusted to pH 6.8, made up to 1 l and sterilized by irradiation.

Example D

Ointment 500 mg of the active compound are mixed with 99.5 g of petroleum jelly under aseptic conditions.

Example E

Tablets

A mixture of 1 kg of active compound, 4 kg of lactose, 1.2 kg of potato starch, 0.2 kg of talc and 0.1 kg of magnesium stearate is compressed in a customary manner to give tablets in such a way that each tablet contains 10 mg of active compound.

Example F

Coated Tablets

Analogously to Example E, tablets are pressed which are then coated in a customary manner with a coating of sucrose, potato starch, talc, tragacanth and colorant.

Example G

Capsules 2 kg of active compound are filled into hard gelatin capsules in the customary manner such that each capsule contains 20 mg of the active compound.

Example H

Ampoules

A solution of 1 kg of active compound in 60 l of double-distilled water is sterile filtered, filled into ampoules, lyophilized under sterile conditions and aseptically sealed. Each ampoule contains 10 mg of active compound.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of treatment for a disease or condition treatable by administration of a kappa-opiate agonist, comprising administering to a patient in need of such treatment the compound N-methyl-N-[(1S)-1-phenyl-2-((3S)-3-hydroxypyrrolidin-1-yl)ethyl]-2,2-diphenylacetamide hydrochloride in a heat-stable crystal form in a daily dose of from about 0.02 to 20 mg/kg.

2. The method of claim 1, wherein the treatment is for an inflammatory bowel disorder.

3. The method of claim 1, wherein the treatment is for postoperative ileus from an abdominal operation.

4. The method of claim 1, wherein the compound N-methyl-N-[(1S)-1-phenyl-2-((3S)-3-hydroxypyrrolidin-1-yl)ethyl]-2,2-diphenylacetamide hydrochloride is in crystal form type IV.

5. The method of claim 1, wherein the compound N-methyl-N-[(1S)-1-phenyl-2-((3S)-3-hydroxypyrrolidin-1-yl)ethyl]-2,2-diphenylacetamide hydrochloride is in a crystal form having a melting point of approximately 121–126° C.

6. The method of claim 1, wherein the compound N-methyl-N-[(1S)-1-phenyl-2-((3S)-3-hydroxypyrrolidin-1-yl)ethyl]-2,2-diphenylacetamide hydrochloride is in a crystal form having a melting point of approximately 121 126° C. and a heat of fusion of approximately 120–128 J/g.

7. A compound which is N-methyl-N-[(1S)-1-phenyl-2-((3S)-3-hydroxypyrrolidin-1-yl)ethyl]-2,2-diphenylacetamide hydrochloride in a heat stable crystal form, prepared by a process comprising reacting 1-[(1S)-3-hydroxypyrrolidin-1-yl]-(2S)-2-methylamino-2-phenylethane with diphenylacetyl chloride at a temperature from −5 to 10° C., wherein the diphenylacetyl chloride dissolved in a solvent is slowly added to the 1-[(1S)-3-hydroxypyrrolidin-1-yl]-(2S)-2-methylamino-2-phenylethane dissolved in the same solvent while maintaining the temperature, and wherein the molar ratio of 1-[(1S)-3-hydroxypyrrolidin-1-yl]-(2S)-2-methylamino-2-phenylethane to diphenylacetyl chloride is from 1:0.75 to 1:1.65, and recrystallizing the crude product obtained from a solvent.

* * * * *